(12) United States Patent
Lo

(10) Patent No.: US 8,557,188 B2
(45) Date of Patent: Oct. 15, 2013

(54) UNITIZED PHOTOCATALYTIC AIR STERILIZATION DEVICE

(76) Inventor: Yang Zhen Lo, Flushing, NY (US)

(*) Notice: Subject to any disclaimer, the term of this patent is extended or adjusted under 35 U.S.C. 154(b) by 599 days.

(21) Appl. No.: 12/685,718

(22) Filed: Jan. 12, 2010

(65) Prior Publication Data

US 2011/0171080 A1   Jul. 14, 2011

(51) Int. Cl.
*B01J 19/08* (2006.01)
(52) U.S. Cl.
USPC ............... 422/186.3; 210/748.01; 210/748.1; 210/748.14; 502/2; 502/439
(58) Field of Classification Search
USPC .......... 422/186.3; 210/748.01, 748.1, 748.14; 502/2, 439
See application file for complete search history.

(56) References Cited

U.S. PATENT DOCUMENTS

| | | | |
|---|---|---|---|
| 6,063,343 A | 5/2000 | Say | |
| 6,135,838 A | 10/2000 | Wang | |
| 6,315,963 B1 | 11/2001 | Speer | |
| 7,303,612 B2 | 12/2007 | Morrow | |
| 2003/0203816 A1* | 10/2003 | Sangiovanni et al. | 502/439 |
| 2004/0040832 A1* | 3/2004 | Kartheuser et al. | 204/157.3 |
| 2005/0186124 A1 | 8/2005 | Fink | |
| 2006/0228275 A1* | 10/2006 | Rutman et al. | 422/186.3 |
| 2007/0243114 A1 | 10/2007 | Morrow et al. | |
| 2008/0073565 A1 | 3/2008 | Jeon | |

\* cited by examiner

*Primary Examiner* — Xiuyu Tai
(74) *Attorney, Agent, or Firm* — Patent Jurist; Georgiy L. Khayet

(57) ABSTRACT

A UV photocatalytic air purifier/sterilizer in which the multiple limited-lifetime components (such as the UV light, UV light electronics, and catalytic portion) of a photocatalytic UV air purifier/sterilizer are packaged together to form a single, handheld, unitized package, designed for easy insertion and removal into an air purifier. The invention may be configured enable maximum air flow through the photocatalytic portions of the device, thus further improving air cleaning efficiency by allowing many volumes of room air to be recirculated through the device and cleaned/purified/sterilized over the course of a day. In a preferred embodiment, the device may package a series of stacked TiO2 coated parallel metal catalytic plates, a UV germicidal lamp with a fluorescent tube form factor, and a UV lamp ballast into a single disposable or recyclable unit. This disposable unit can be easily clipped into a motorized air purifier unit designed for rapid servicing.

19 Claims, 9 Drawing Sheets

UNITIZED PHOTOCATALYTIC AIR STERILIZATION DEVICE

BACKGROUND OF THE INVENTION

1. Field of the Invention

The invention is in the general field of air purification and sterilization devices. In particular, the invention is more specifically in the area of ultraviolet (UV) mediated air purification and sterilization devices, in particular photocatalytic oxidation devices.

2. Description of the Related Art

The interior air in dwellings and vehicles is often unsatisfactory or unpleasant due to the presence of airborne contaminants such as dust particles, allergens (e.g. pollen, pet dander, dust mite feces, mold spores), as well as living bacteria or bacterial spores, living molds or mold spores, viruses, and volatile organic compounds (VOC). As a result, there has been a significant amount of interest in developing improved devices and methods for removing these various contaminants.

Although filters, such as high efficiency particulate air (HEPA) filters can remove some of the particulate contaminants, many HEPA filters still allow smaller particles, such as particles of 0.3 micrometers in diameter or less, to pass through the filter. Thus the industry has turned to secondary systems, such as photocatalytic oxidation (PCO) systems. These systems typically generate hydroxyl radicals and super-oxide ions by exposing semiconductor particles to UV light rays, usually in the presence of at least trace amounts of moisture from the atmosphere. These hydroxyl radicals and super-oxide ions in turn react with the airborne contaminants and can oxidize the contaminants, ideally breaking the contaminants down into simpler molecules such as carbon dioxide and water, and at least neutralizing the biological capability (i.e. sterilizing) any living airborne spores, bacteria, moulds, or viruses. Additionally, the allergenic effect of non-living allergens can also be reduced or eliminated.

As a result, a number of different types of photocatalytic UV air purifiers/sterilizers are presently on the market. Although effective, these devices are often difficult to maintain. The UV light sources, electronics, and photocatalytic surfaces used in these devices often have a limited lifetime (often a year or less). As a result, service and replacement of these various limited-lifetime components can place a burden on unskilled users. Air purifiers must be disassembled, UV lighting sources extracted from catalytic elements and their support electronics, the defective part removed, a new part added, and then the entire unit must be reassembled, often with the use of tools. As a result, due to the inconvenience of servicing, many of these purifiers/sterilizers often run using out-dated components running at substandard levels of efficiency.

Another problem with prior art devices is that many photocatalytic UV air purifiers force the air through complex catalytic fabric or catalytic mesh structures that can act to limit air flow. As a result, even though the actual effectiveness of the photocatalytic UV air purifier on any given pass of the air through the device may be high, the net effectiveness of the air purifier may still be inadequate. This is because due to the low flow rates, only a small amount of the air in the room or vehicle may be processed in any given period of time.

Unfortunately, in most air purifier uses, the air is recirculated. That is, the devices are set up so that "dirty" air from the room is processed into "clean" air, and this clean air is then placed back into the room with the remaining dirty air. Thus due to mixing, the effectiveness of the clean air is thus reduced by the large amount of "dirty" air. Thus low air flow also causes many prior art photocatalytic UV air purifiers/sterilizers to operate at substandard efficiency as well.

As a result, further improvements in the design of photocatalytic UV air purifiers are desirable.

BRIEF SUMMARY OF THE INVENTION

Here, an improved UV photocatalytic air purifier/sterilizer is disclosed in which the multiple limited-lifetime components of a UV photocatalytic air purifier/sterilizer, such as the UV light source, the electronics used to manage the UV light source, and the catalytic elements are packaged together to form a single, handheld, unitized package. This unitized package is designed for easy insertion and removal into an air purifier, ideally without use of additional tools.

The present invention also is designed to maximize air flow through the photocatalytic portions of the device, thus further improving sterilizer efficiency by allowing many volumes of room air to be recirculated through the device and cleaned/purified/sterilized over the course of a day.

DETAILED DESCRIPTION OF THE INVENTION

At their heart, air purification and sterilization devices represent a series of engineering compromises. The devices should ideally maintain high air flow, so as to be able to continually process the air in a room or dwelling at high enough rates so as process most of the air in a room at least multiple times over the period of a day. The filtration and sterilization of the device should be high, but not at the expense of reducing the air flow rate to the point where the device's ability to process air is insufficient. The devices should run quietly, Air purification and sterilization devices typically contain multiple components, each with a limited lifetime. Air filtration components can include HEPA filters, pre-filters, activated carbon filters, and other types of filters, which eventually will become clogged with many small air particles or otherwise inactivated and must eventually be replaced. The limited-lifetime UV photocatalytic (here called "sterilizing" to distinguish this function from a simple filter function) components can include UV light sources and electronic power supplies, such as the electronic UV germicidal lamps and ballasts (or other electronic circuitry) used to produce UV light. Even the catalytic surfaces, used in conjunction with UV light and often moisture and/or oxygen in the air to create anti-microbial oxidizing agents, can eventually become "poisoned" or inactivated by airborne dust and chemicals, and can lose effectiveness.

As previously discussed, the invention is designed to overcome these difficulties by providing a unitized device that packages the limited lifetime components of a photocatalytic air purifier/sterilizer, namely the UV light source, limited-lifetime electronics (such as a ballast) that manage or power the UV light source, and the catalytic support, into a single handheld unit. This combined unit can ideally then be easily inserted or removed from an air purifier unit in a single operation, ideally without the need for extra tools.

The invention is also designed for maximum air flow, ideally allowing the air in a room or vehicle to be recirculated many times over the course of a day, thus rapidly diluting the concentration of unwanted airborne contaminants.

Nomenclature: For brevity, the UV photocatalytic devices will often be referred to in the alternative form as UV air sterilizer devices, UV sterilization devices, or even as sterilizers. Again, all applications of the use of hydroxyl radicals and super-oxide ions for breaking down or destroying a wide variety of different contaminants, including both living and non-living contaminants, is encompassed by this "sterilization" term.

Figure 1:
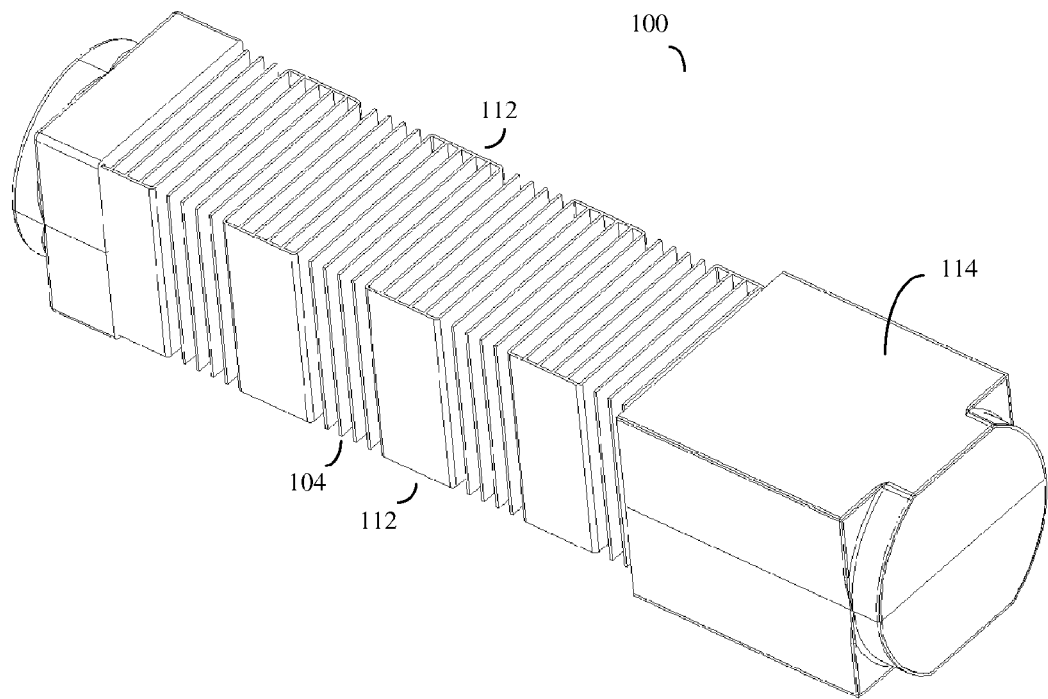
FIG. 1 shows a 3D overview of the exterior of the unitized UV photocatalytic air sterilization device.
Figure 1:
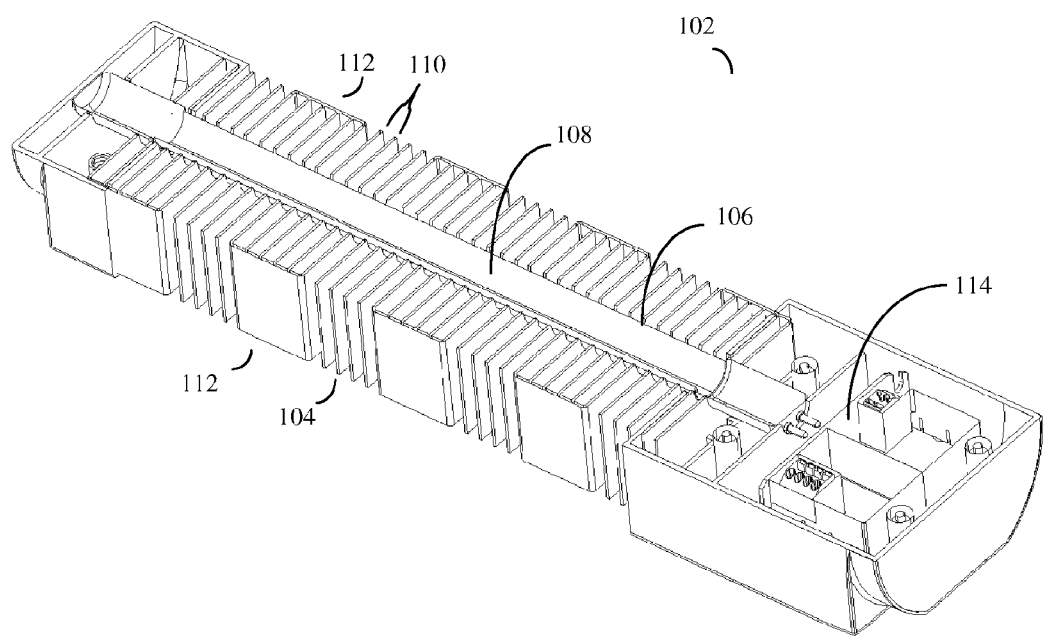

FIG. 1 shows an overview showing the exterior of one embodiment of the unitized UV air sterilization device (100), and a cutaway view of the interior of the same device (102) In this figure, the device is shown with a plurality (here 44) of metal (aluminum) plates (104) stacked parallel to each other. Although these plates will often be referred to in this specification as metal plates or catalytic metal plates, in fact there is no requirement that the underlying material of the plates be metal at all. In alternative configurations, other non-catalytic structural materials, such as plastic or metal coated plastic, may also be used. For simplicity however, since such plates are often made of metal materials such as aluminum or steel, these plates will be otherwise referred to in this specification as "catalytic metal plates".

In the particular embodiment exemplified by FIG. 1, each catalytic metal plate has a square shape with dimensions of roughly 70 mm×70 mm×0.5 mm, and each metal plate also has a central hole (here circular) (106) about 15 mm in diameter. One or more UV light sources (here a single UV germicidal lamp in a common fluorescent light tube form factor is shown) (108) runs in the center of the device through the various central holes. The metal plates are stacked with a separation of about 5 mm between plates, and all of the metal plates have roughly the same size and shape. The metal plates are typically coated with a UV light activated catalyst, which are often particles of semiconductors such as titanium dioxide. Due to the configuration of the plates relative to the UV light source, which enables the UV light source to shine on both sides of the plates, both plates are typically coated with the UV light activated catalyst, effectively doubling the efficiency of this design over prior art devices that used one side of the plate as a UV activated catalyst.

As previously discussed, when activated by UV light from the central light source(s), the catalytic particles can in turn react with trace amounts of moisture from the air, and/or oxygen from the air, and produce oxidant molecules (e.g. hydroxyl radicals, super-oxide ions) capable of destroying microbes (e.g. bacteria, molds) and viruses often carried in microscopic airborne particles. Such catalytic particles can also be useful for neutralizing unwanted airborne allergens (e.g. pollen, pet dander, dust) volatile organic compounds (VOC) as well. As previously discussed, typically both sides of the metal plates will be coated with semiconductor material in order to maximize sterilization, allergen breakdown and VOC neutralization efficiency. As previously discussed, the term "sterilization" will here also encompass allergen and VOC neutralization capability as well.

The separation between the catalytic metal plates (110) is typically chosen to be a balance between maximizing the amount of air flow past the plates, and maximizing sterilization efficiency. As the separation between the catalytic metal plates decreases, two undesirable things happen. One undesirable effect is that there is a proportionally lesser amount of UV light flux available to each plate, since typically only the UV light source originating from that portion of the light source between the gap between the plates will be available to contribute UV light. The other undesirable effect is that there will be a greater surface area of the catalytic metal plates available to obstruct air flow. This can result in both higher noise generation, and also a decrease in the amount of air the device can process over any period of time. The beneficial effect of a lesser separation, however is that the chance of a microbial or viral particle contacting the catalytic surface of the catalytic metal plate will increase as the gap between the plates decreases. In general, for the purposes of this invention, gaps (110) in the 1 to 20 mm range, often in the 2 to 10 mm range, preferably between 3 to 7 mm, and here drawn as 5 mm separation have been found to offer a good compromise between optimizing air flow and sterilization efficiency.

The device has a number of other design features intended to optimize air flow. As can be seen in FIG. 1, the catalytic metal sheets are connected by their edges to support plates (112), so that the catalytic metal sheet (104) is connected by one edge side of the square metal catalytic sheet to the support plate (112) at a roughly 90 degree angle (perpendicular). In this embodiment, six catalytic metal sheets are connected to each support plate, and the arrangement of the support plates is such that the support plates are alternately positioned with one support plate (112) on one side of the catalytic metal plates, then another support plate on the opposite side of a different group of metal plates, so that although ultimately, all catalytic metal plates are supported by attachment to their particular support plate, the arrangement of support plates is such that there is never a full "wall" of support plates capable of totally restricting air flow from any angle. In this embodiment, for example, at most only about 50% of one side is obstructed to air at any given time. The advantages of this approach will be discussed in more detail in the discussion of FIG. 9.

Although the support plates (112) need not be themselves covered with a catalytic material, there is some benefit to doing so because the overall catalytic surface area of the unitized air sterilizer device will increase somewhat. In some embodiments, it may be useful to first manufacture all plates (e.g. both support plates and catalytic plates) and support plates out of a metal, (such as aluminum), plastic, or metal coated plastic, and then apply the semiconductor catalyst in a second operation by a spraying or dipping process, in which case often the support plate will be coated with the semiconducting material as well.

Although the catalytic metal plates (104) are shown in this embodiment as being square in shape, other shapes, such as rectangular shapes, triangular shapes, pentagons, etc. may also be used. Ideally the shape and central hole (106) for the UV lamp (108) will be chosen as to efficiently utilize the light emitted by the UV lamp. Thus in a preferred embodiment, the plates will have rectangular shape close to that or equal to that of a square. The actual size of the plates may also differ, and may be as low as 10 mm in diameter (or per side) for some miniaturized applications up to 500 mm by 500 mm in diameter (or per side) or greater for purifying the air in extremely large rooms. The number of individual plates will typically vary from as few as 2 to as many as 1000 or more, with plate numbers in the 10 to 300, and still more preferably in the 20 to 100 range being preferred.

Modern UV light sources, such as UV germicidal lamps (again often made in a fluorescent tube form factor), often have use lifetimes of about 10,000 to 20,000 hours, which coincidentally is often roughly similar to the use lifetime of the electronic circuits, such as ballast circuits, used to drive these UV light sources. Indeed, as previously discussed, even the semiconductor catalyst coating itself has a finite lifetime because gradually it can become contaminated or "poisoned" by a gradual buildup of various compounds and particles from the air.

As previously discussed, one problem associated with prior art UV air sterilization devices was the problem of maintenance. Typically each individual element of the device, such as the UV light source, the electronics that drive the UV light source, and the catalytic surfaces were designed as individual stand-alone devices, and installed into larger air purifier devices in a way that made maintenance difficult. A user would have to perform a first maintenance operation to open up the device and extract the UV light source from the UV light source holder, catalytic material, and power supply electronics. Then perform a separate operation to service the power supply, and a third operation to service the catalytic material.

By contrast, if this prior art practice of producing discrete components is dropped in favor of producing a new type of unitized air UV sterilizer device, a number of distinct advantages result. To begin with, user servicing of the air purifier device that holds the UV light source, UV light source electronics, and catalytic material can be greatly simplified. For example, in one embodiment, a simple "clip in" (and perhaps disposable or recyclable) air UV sterilizer device can be produced that can be easily replaced by the user in a simple one-step, and ideally tool-free, operation.

An additional advantage of this unitized UV photocatalytic light source, electronics, catalytic device (air UV sterilizer device) is that it can greatly simplify the design of the larger air purifier device that holds the air UV sterilizer device as well. For example, if the electronics section or module of the unitized air UV sterilizer device (114) is designed to handle typical international AC voltages (which typically run from about 100 to 240 volts, at either 50 or 60 Hz), then a single type of air purifier device (that holds the air UV sterilizer device) can be inexpensively constructed that can work in all countries worldwide, irrespective of local AC voltages. This can lead to manufacturing efficiencies, as well as sales, marketing, distribution and servicing efficiencies as well. In FIG. 1, electronics section (114) holds the electronics used to drive the UV light source (108).

As previously discussed, the "metal" plates (104) will typically be converted to catalytic metal plates (or catalytic plates) by coating with a suitable semiconductor, such as titanium dioxide ($TiO_2$) or other material(s), chosen for their ability to accept UV light, water molecules, and alternatively oxygen as input, and produce sterilizing oxidizing molecules as output. Although titanium dioxide is given as an example, this example is not intended to be limiting, and other types of semiconducting particles may be used. Additionally other types of materials, such as water absorbing agents, other antimicrobial materials, and other chemicals (i.e. binders, preservatives, reflective materials, etc.) may also be used. Examples of suitable catalytic semiconductors and other materials useful for this purpose include the hydrophilic agent(s) titanium dioxide, silver/copper/rhodium materials and methods taught by Fink et. al., US application 2005/0186124, the contents of which are included herein by reference.

Other suitable catalytic materials and methods are taught by the materials and methods of Morrow et. al., US application 2007/0243114, the contents of which are incorporated herein by reference.

The wavelengths of the UV light sources (UV germicidal light) will usually be in the UVC wavelength of around 100 to 280 to 300 nm. At the longer wavelength end, the maximum energy (maximum wavelength) of the UV light useful for this purpose is about 385 nm, which represents the band gap energy of semiconductor catalysts such as $TiO_2$. Often wavelengths such as 245 nm and/or 185 nm may be used.

For example, Morrow teaches the utility of coating no more than 5% of the surface of a reflective metal with photocatalytic particles in order to maintain the UV reflective characteristics of the underlying reflective material (such as the non-catalytic metal base), and Morrow wishes to have the UV light bounce back and forth many times within Morrow's reflecting cavity.

These methods may also be useful in some embodiments of the unitized UV photocatalytic device as well. This is because although the disclosure's parallel metal plates do not form a completely enclosed UV reflective cavity, the relatively large size (e.g. 70×70 mm) of the plates coupled with their typically close spacing (e.g. 5 mm) means that the UV light may also bounce back and forth between an first plate and a second plate may times before the UV light is either absorbed or else escapes through the open sides at the edge of the plates. Thus Morrow's methods, such as the utility of using water absorbing materials (such as silica gel or other dielectric material) on the surface of the reflecting cavity to help promote the desired UV stimulated catalytic activity can be useful in some embodiments of the unitized UV photocatalytic device as well.

Figure 2:
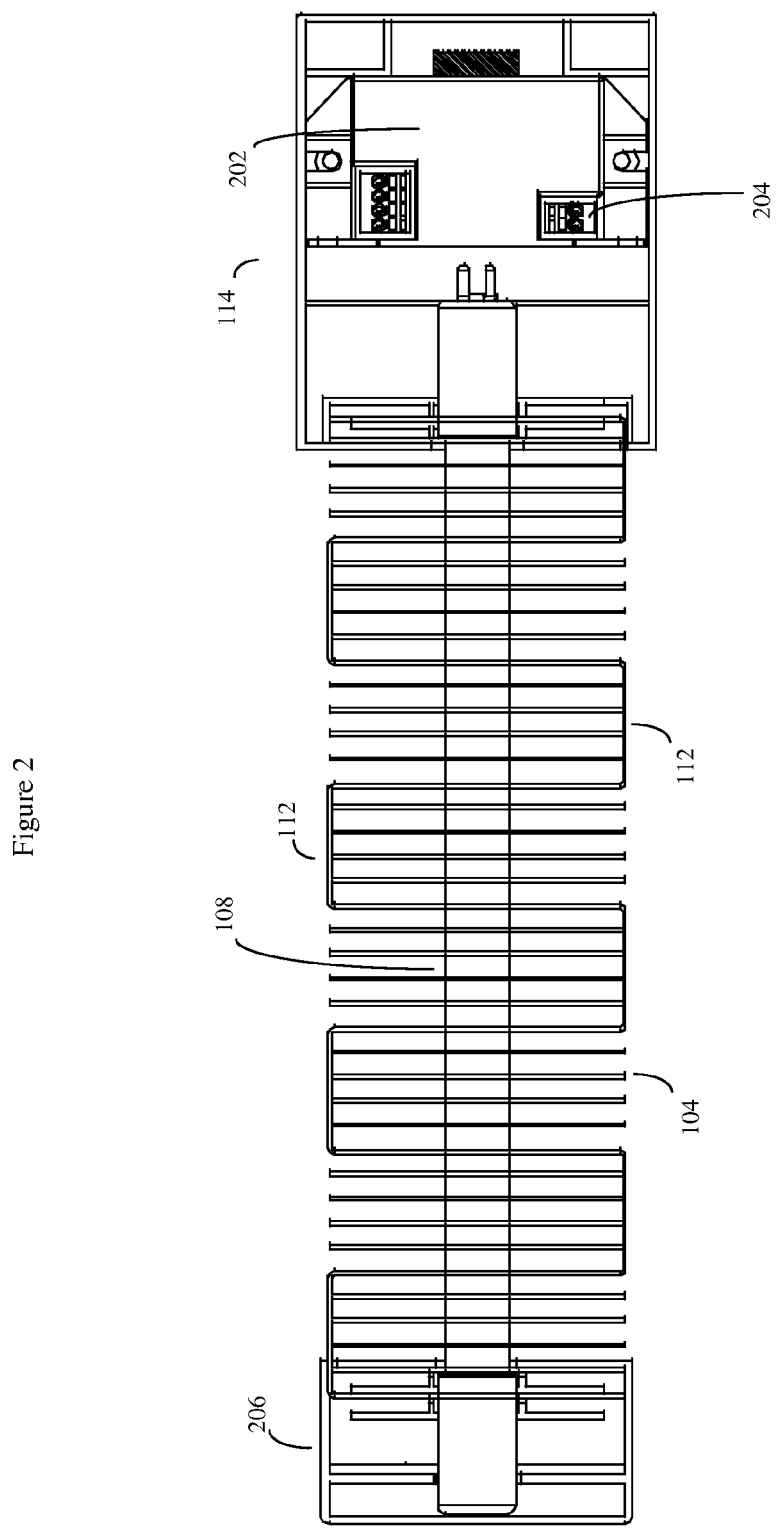
FIG. 2 shows a cut away view of the interior of the unitized UV photocatalytic air sterilization device.

FIG. 2 shows a top cut away view of the interior of the unitized UV air sterilization device previously shown in FIG. 1 (102). Here the UV light source, here depicted as a single linear UV germicidal lamp with a fluorescent tube form factor (108) is shown, as well as a cross section of the catalytic metal plates and support plates. On the right, the section of the case that holds the power electronics needed to drive the UV light source (114), such as ballast (202) and appropriate power connectors (204), are shown. On the right, the holder (206) that caps the end of the device and protects and holds the end of the UV light source is shown.

Figure 3:
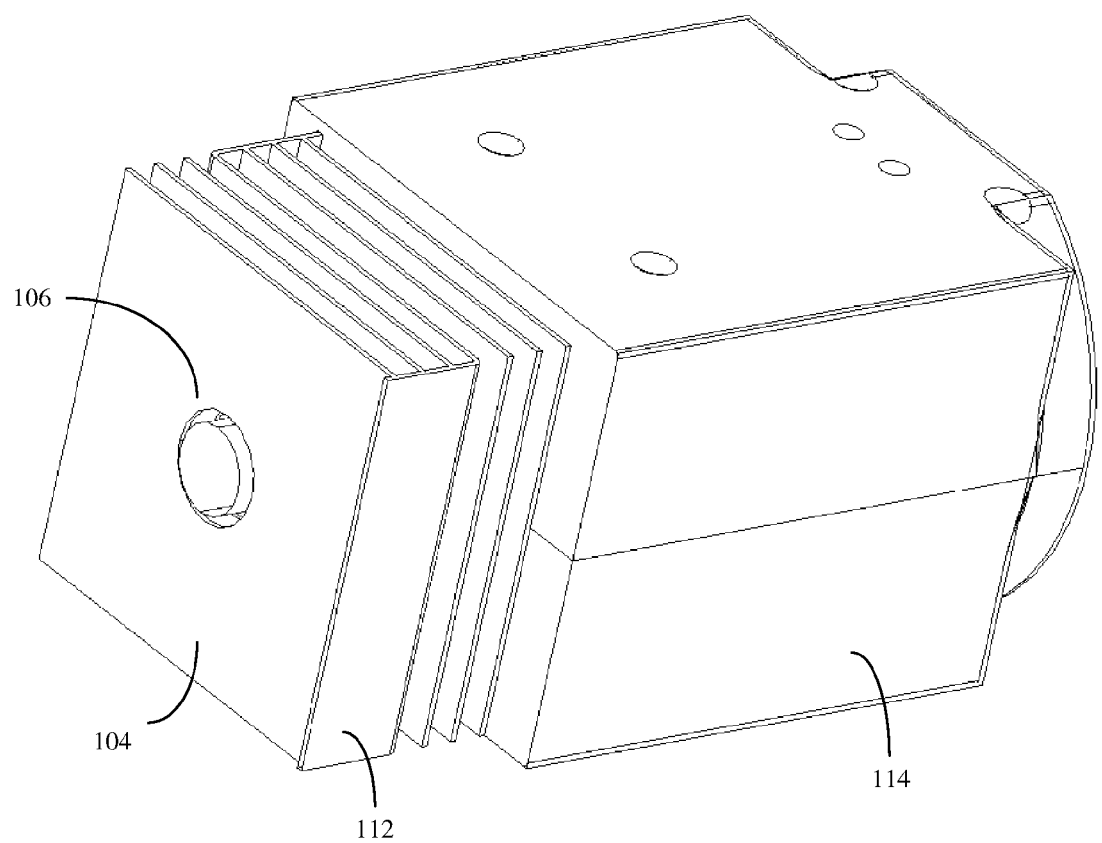
FIG. 3 shows a 3D cross section of the unitized UV photocatalytic air sterilization device, focusing on the details of one of the catalytic plates.

FIG. 3 shows an alternate cross section through the device, exposing the details of one of the catalytic metal plates (104) and its central hole (106). Note that one edge of the catalytic plate (104) is attached to a support plate (112) at a right angle.

The portion of the device that holds the electronics (114) is also shown with the top of the electronics case attached.

Figure 4:
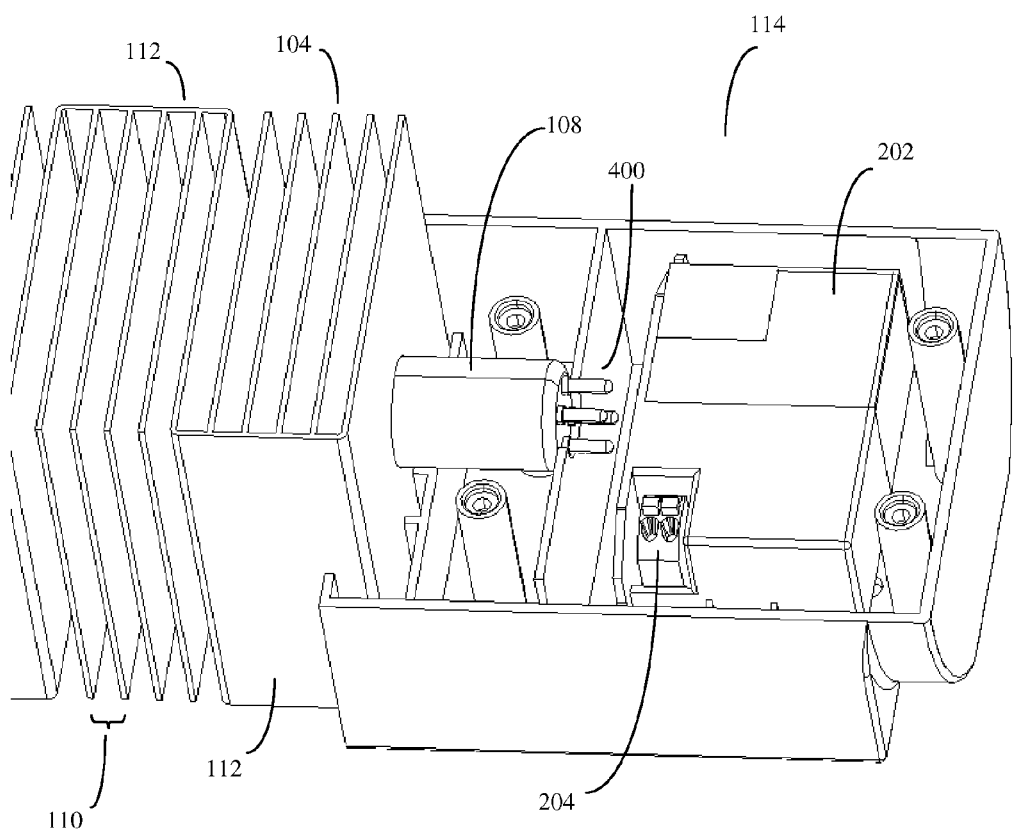
FIG. 4 shows a 3D detail of the electronics portion of the unitized UV photocatalytic air sterilization device, in which the top portion of the electronics module has been removed, exposing some of the details of the circuitry.

FIG. 4 shows a detail of the electronics portion of the unitized device (114), in which the top has been removed in order to show additional details. Here the UV light source (108) is again shown as a single UV germicidal lamp with a fluorescent light tube form factor that has been inserted into the central holes of the parallel catalytic metal plates, and the power plugs of this light source (400) are protruding into the electronics portion. (For clarity, the connecting wires and plugs are not drawn.) In this example, the electronics again includes ballast (202) and suitable power connecting plugs (204). Typically prongs or jacks from an external purifier device (not shown) will supply external power to these power connecting plugs (204). This can be seen in more detail later in FIG. 8 (812).

Figure 5:
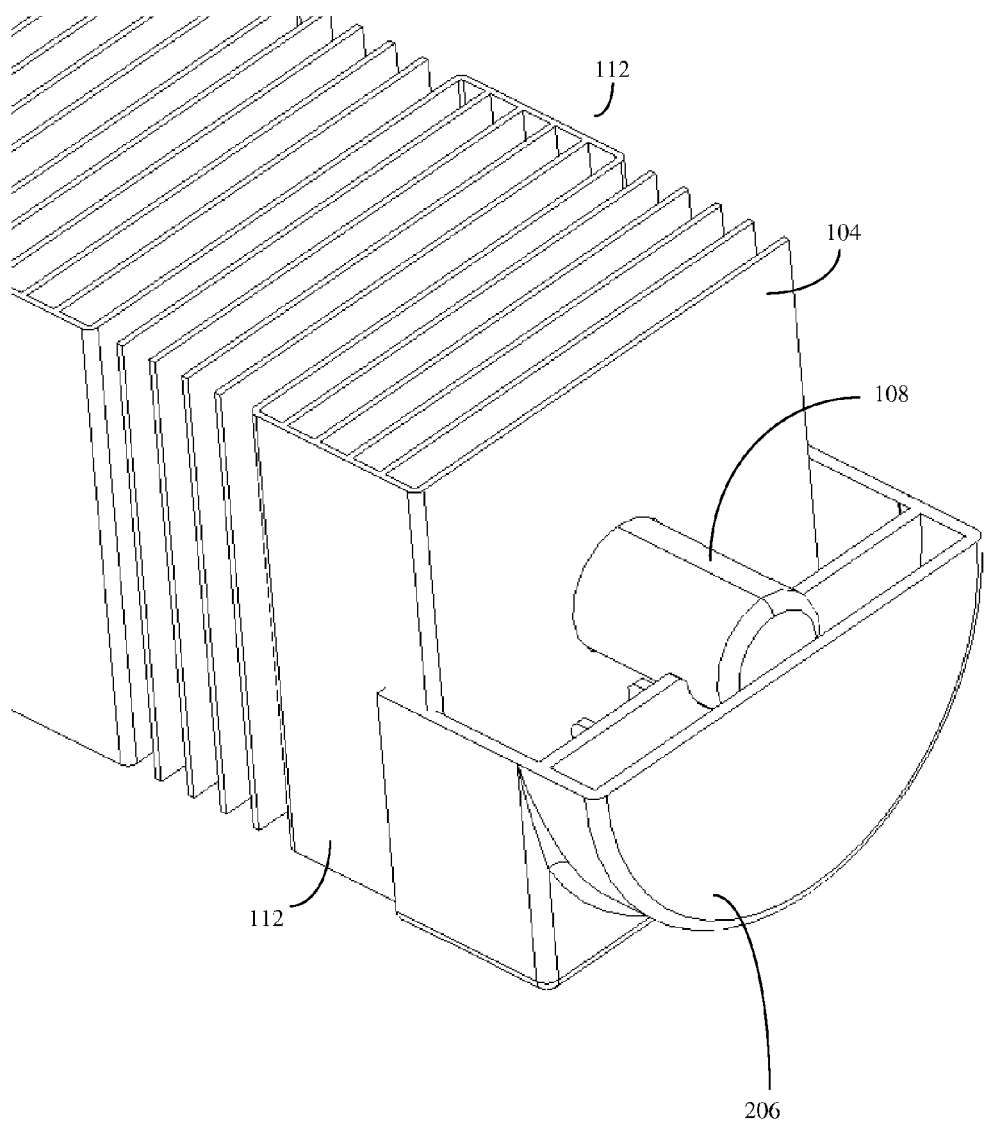
FIG. 5 shows a 3D detail of the opposite "holder" end of the device, in which the top portion of the opposite end has been removed exposing some of the details of the UV light source.

FIG. 5 shows a detail of the holder end of the device (206), showing the distal end of the UV light source (108) being capped and protected by the holder. Again, the top portion of the holder has been cut away to allow for better visualization.

Usually, the unitized UV air sterilization devices (100) will be mounted on the interior of a larger air purifier device. Often it may be useful to mount the unitized UV light sterilization devices (100) using clips or other type of holding fixture that can allow the sterilization devices to be easily mounted to an interior wall of the air purifier device, and removed by unskilled users without the need to use additional tools.

Figure 6:
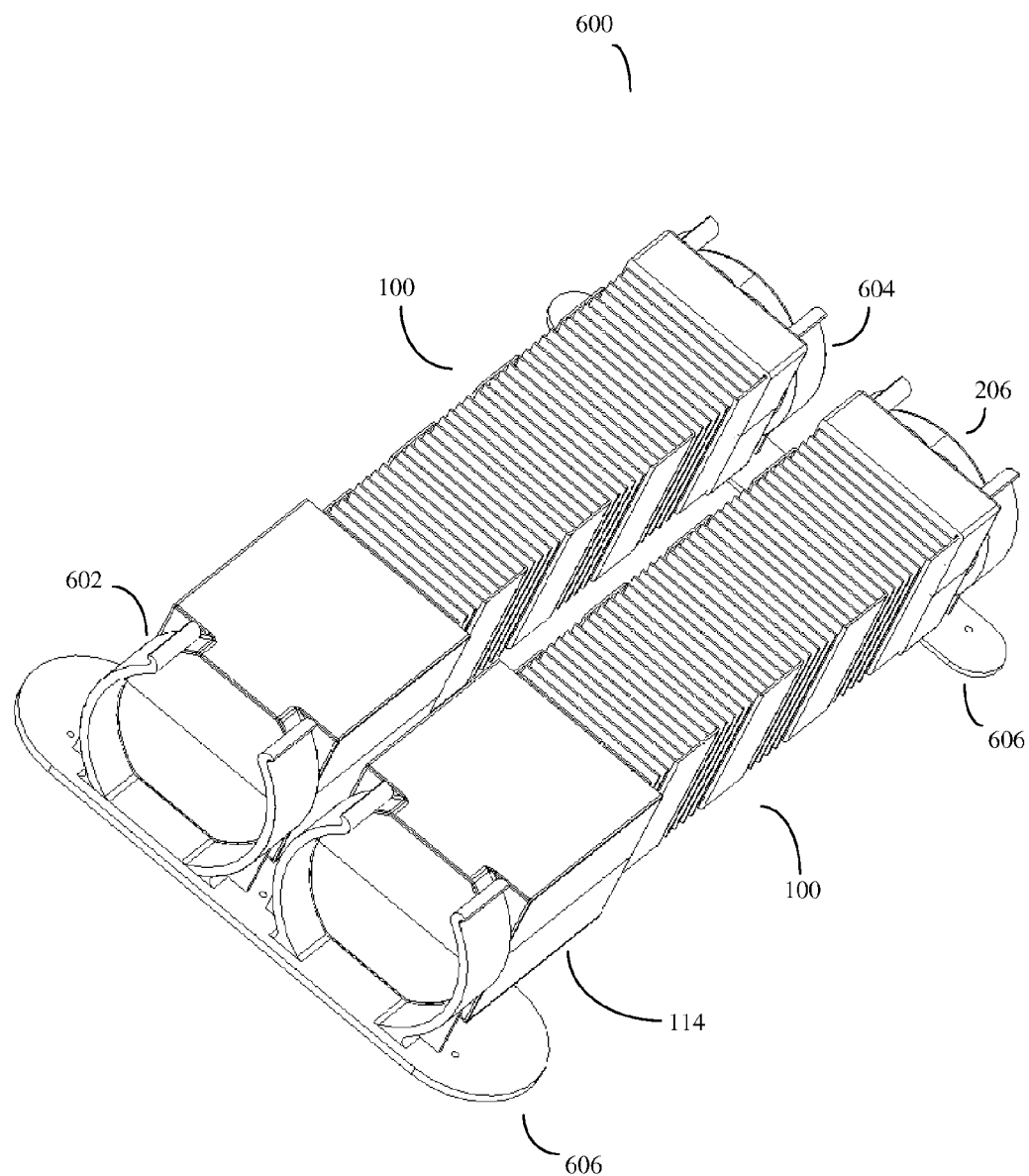
FIG. 6 shows a 3D view of a clip fixture which can be used to attach two of the unitized UV air sterilization devices to the inner wall of a larger air purifier unit.

FIG. 6 shows a 3D view of a clip fixture (600) that can hold two unitized UV air sterilization devices (100). In this embodiment, the clip fixture can hold the unitized UV air sterilization device(s) by a first clip (602) that attaches to the electronics portion (114) of device (100), and a second clip (604) that attaches to the holder portion (205) of device (100). Clip fixture (600) may additionally contain wall mounting brackets (606) to attach the fixture (600) and attached unitized UV air sterilization devices (100) to an interior wall of an air purification device.

Figure 7:
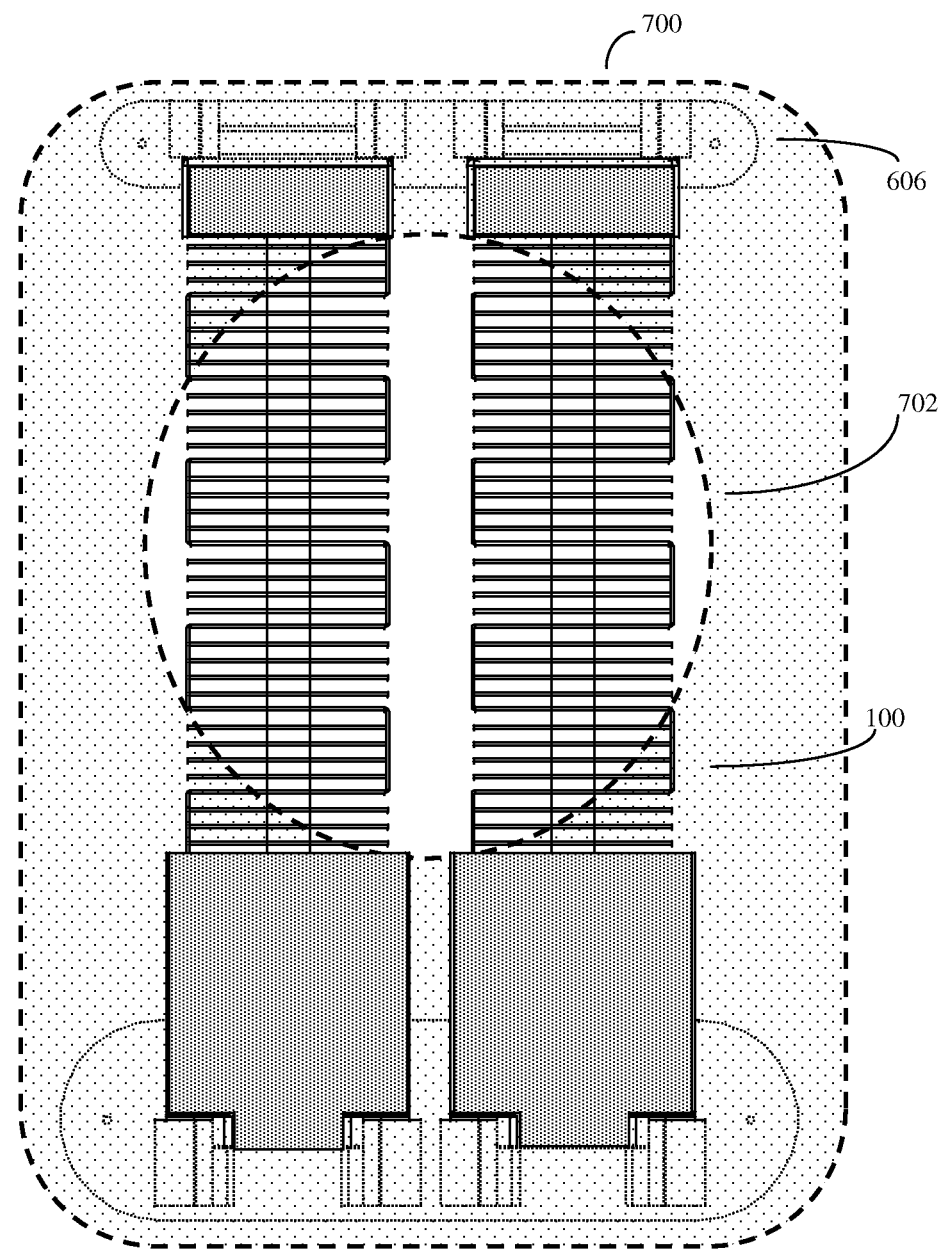
FIG. 7 shows a top view of this clip fixture.

FIG. 7 shows a top view of the same dual clip fixture, here shown mounted on an interior wall (700) of an air purifier device (800). This interior wall (700) will usually have one or more holes (702) so that air (often driven by the force of a motor driven air blower), may be driven to pass through the slots of the unitized UV air sterilizer devices (100) and out through the other side. Here the dual clip fixture is drawn with dotted lines in order to better distinguish the fixture from the unitized UV air sterilization device (100).

Note that one aspect of this design is that rather than attempting to sterilize 100% of the air in one pass through the air purifier and the unitized UV air sterilization device, the design instead emphasizes high air flow, so that the air may pass through the air purifier many times over the course of a day, each time reducing the amount of microbial or viral particles, allergens, or VOC present in the air.

Figure 8:
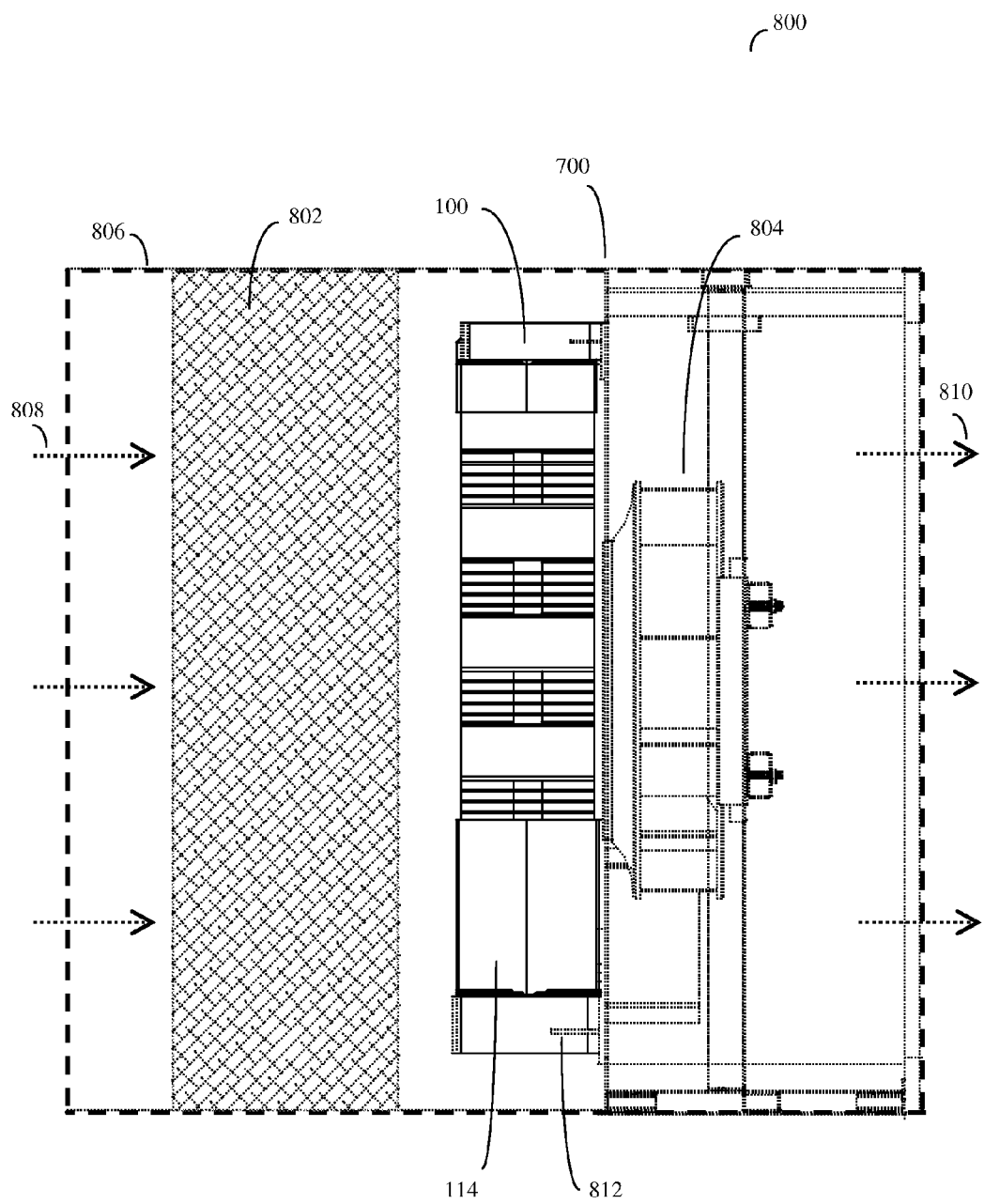
FIG. 8 shows the unitized UV photocatalytic air sterilization device(s) mounted inside of a larger air purifier unit, equipped with an air filter (such as a HEPA filter), and a motor driven air blower.

Parts of FIG. 7 may be best understood by also comparing FIG. 7 with FIG. 8. In this embodiment, an air filter, such as a HEPA filter (802), may optionally be mounted on top of (or in front of) the unitized UV air sterilizer devices (100), clip fixture, and wall (700), and a motor driven air blower (804) may be mounted behind (or in back of) the wall (700). The sides of the wall (700) will normally be covered by an enclosure (806) that forces the outside air (808) to travel through the air filter (802), the unitized UV air sterilization device (100), the hole (702), before allowing the now purified and partially sterilized outside air (810) to exit the air purifier device.

FIG. 8 shows an alternate view of an embodiment of the air purifier device (800), showing more details of the optional air filter (802), the unitized UV air sterilization device(s) (100), and the motor driven air blower (804). Here the power plugs or prongs (812) that supply power to the electronics module (114) of the unitized UV air sterilization device (100) are also shown (812).

As previously discussed, the air purifier unit (800) consists of an enclosure (806) with a front air intake, often through an optional air filter such as a HEPA filter (802) that removes larger air particles. After passing through the optional filter, the air then passes through a wall one or more holes (702) in interior wall (700). However before doing so, in this embodiment, the air also flows through the catalytic plates (104) of the unitized UV sterilization device (100).

To do this, the mounting clips (602) hold the one or more unitized UV light sterilization devices (100) are mounted on wall (700), and the unitized UV light sterilization devices themselves (100), are then clipped to the mounting clips. To force the air to move, in this in this embodiment, a motor driven air blower (804), mounted on the opposite side of wall (700) and hole (702) operates to suck air from the outside (808) through the optional HEPA filter (or other type of air filter) (802), then through the unitized UV light sterilization devices (802), and then through the hole in the wall (702) and out (810) the other side of the motor driven air blower (804).

As a result of this process, the airborne contaminants, such as the VOC, allergens, microbes, and viruses are neutralized by the action of the UV activated catalyst as the air passes through the series of metal catalytic plates (104).

Figure 9:
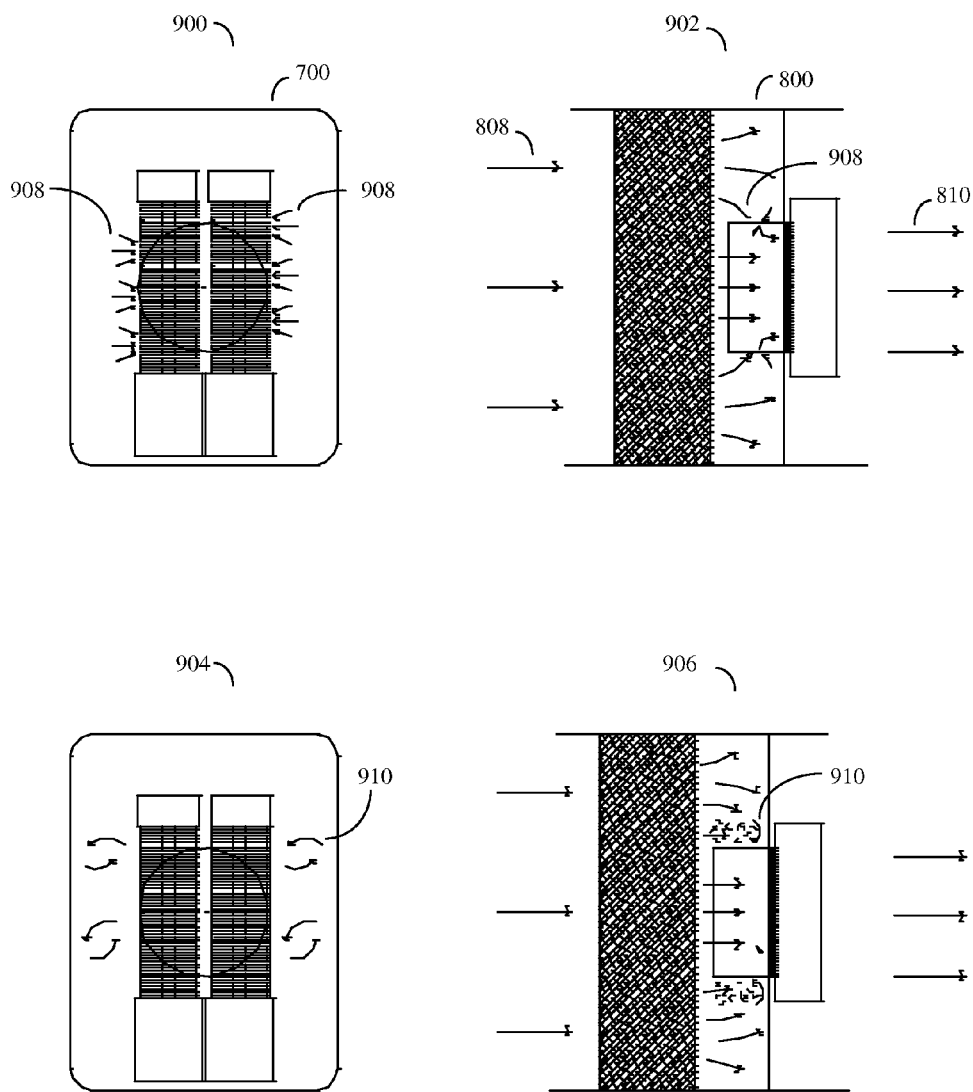
FIG. 9 shows a diagram of the air flow passing through two unitized UV photocatalytic air sterilization devices mounted inside of a larger air purifier unit, showing that greater air flow is possible if the support plates on the unitized UV photocatalytic air sterilization device are arranged so as never to create a full barrier to the free flow of air in any direction.

FIG. 9 shows various drawings of the air purifier wall (700) and overall air purifier device arrangements previously shown in FIGS. 7 and 8, showing the air flow through the device(s) in both the preferred embodiment (900), (902) where the support plates (112) are arranged so as to never to create a major block to air flow from any direction, and a less preferred embodiment (904), (906) in which the support plates (112) are arranged so as to create a major block to air flow from one direction.

Note that in the preferred air purifier configuration, air may pass through the catalytic plates (104) in the unitized UV air sterilizing device (100) from both the side of the sterilizing device that faces the HEPA filter, and from the sides of the sterilizing device that are at right angles to the HEPA filters, because at most only about 50% of these right angle sides are blocked by the support plates (112). Thus air can flow in through gaps between the catalytic plates (104) from the sides as well as from the top (908). This results in a greater amount of air flow through the unitized UV sterilization device (100).

By contrast, in the less preferred embodiment (904), (906), in which all of the support plates (112) are arranged on the same side of the device (100), the support plates will act to substantially limit the free flow of air into the unitized UV sterilization device (100) from at least the side of the device facing at a right angle to the optional HEPA filter. Although air can still enter the gaps between the catalytic plates (104) from the top or filter side of the sterilization device (100), the total amount of air flow is substantially less, because the air from the side is blocked by the support plates (112). This blocked air is shown as (910).

Calculations:

In order to illustrate the improved catalytic efficiency of this device over prior art devices, such as the device of Morrow et. al. (U.S. Pat. No. 7,303,612, the contents of which are incorporated herein by reference), a few calculations will be given.

If an alternative prior-art box shaped structure with dimensions 70 mm×70 mm×230 mm was produced with a central UV lamp, then the total surface area of the interior of this box that would be available for catalytic activity would be the four walls of the box alone (since the top and bottom would presumably have to be open for air flow). This would be 70×230×4=64,440 square millimeters. (Keep in mind that in the Morrow design, these four catalytic walls are solid, and totally obstruct air flow past these walls).

By contrast, the invention, using the embodiment shown in FIG. 1, would have an effective catalytic area, per plate, of 70 mm×70 mm (plate dimensions)×2 (sides per plate)−$\pi r^2$ (the diameter of the inner circle, which is 3.14*(15/2)$^2$ or 422 mm2)=9,378 square millimeters per plate. Since in this example, 44 plates are placed in the same 230 mm length, the total surface area of the device in FIG. 1 is thus 44*9,378=412,632. Thus, relative to the prior art design of Morrow, the present invention has 6.40 times greater surface area. Note also that in the FIG. 1 design, none of the sides of the device are completely obstructed, and thus air may flow from all sides.

Thus the invention both has a larger catalytic area, and it also impedes air flow less than the Morrow device. Neglecting the obstructing effects of the UV light source, the Morrow device has an effective air opening (free air flow area) of only 70×70 mm (i.e. the top or bottom of the device), which is 4,900 square millimeters. By contrast, the embodiment shown in FIG. 1 has an effective air opening (free air flow area) of at least 70×230 mm (minus 44×70×0.5 mm if the plates are 0.5 mm thick) or 16,100−1,540 or 14,560 mm.

A high air flow is of course critical to the proper operation of the device. For example, a device with a very high catalytic surface area, but no openings to allow air to flow, will of course be useless. In general, the amount of air flowing past an opening will be proportional to the surface area of the opening, times the flow velocity of air (often expressed in Cubic Feet per Minute or CFM).

Assuming equal UV light flux, the net catalytic efficiency will roughly be proportional to the amount of catalytic surface and the amount of free air flow past the catalytic surface.

Catalytic Efficiency=Catalytic area*free air flow

And since free air flow=free air flow area*CFM then:

Catalytic Efficiency=Catalytic area*free air flow area*CFM

Here, the differences between the embodiment shown in FIG. 1 and the prior art Morrow device become still more striking. Note that when comparing differences between units otherwise similarly situated, the CFM value cancels out, and we can just compare Catalytic area*free air flow area.

The Morrow device has an overall efficiency of catalytic surface area*free air flow area of 64,440*4,900=315,756,000 mm$^2$ catalyst*mm$^2$ airflow.

By contrast, the device in FIG. 1 has an overall efficiency of 412,632*14,560=6,007,921,920 mm$^2$ catalyst*mm$^2$ airflow.

The ratio of the catalytic efficiency of the two units is thus roughly 19:1 in favor of the device shown in FIG. 1. This catalytic efficiency measurement can also be a useful way to compare the invention with prior art meshwork or fabric devices, since although some of these alternative meshwork or fabric devices may have a larger catalytic surface area, they will also have a far smaller free airflow area, and/or be exposed to a far smaller amount of incident UV light flux. Thus the overall catalytic efficiency of these prior art devices is again sub-optimal (as compared to the invention) due to reduced air flow and lesser UV light flux.

Other Embodiments:

Although some specific embodiments of the invention have been disclosed, these embodiments and examples are not intended to be limiting. Other embodiments will also be clear to those skilled in the art. For example, although the particular embodiments discussed here disclosed use of the unitized UV air sterilization device in the context of an air purifier device that also used other filters, such as HEPA filters, to pre-purify the air, use of such filters is not obligatory. Thus in alternative embodiments of the invention, such air filters may be omitted, or alternatively different types of air filters may be used.

Further, although some embodiments of the invention may be configured with relatively wide spacing between the catalytic elements (e.g. catalytic plates) to enable high levels of air flow, this is just one of many potential embodiments. In other embodiments, the requirement for high air flow may be reduced or dropped. In this case, alternative catalytic elements employing foams, meshes, fabrics, narrowly spaced catalytic plates, or other lower air flow configurations may also be used.

The invention claimed is:

1. A unitized photocatalytic air sterilizer device, comprising:
a plurality of stacked parallel catalytic plates, each said catalytic plate having a central opening, thus creating a plurality of stacked central openings;
at least one electronic UV light source positioned inside said plurality of stacked central openings so that said at least one electronic UV light source spans said plurality of stacked central openings;
electronic circuitry capable of powering said at least one electronic UV light source;
wherein said catalytic plates comprise a non-catalytic base material and a catalytic semiconductor outer coating;
said catalytic semiconductor outer coating being chosen so as to catalytically react with UV light source energy produced by said at least one electronic UV light source, trace amounts of water vapor in the air, and produce oxidizing chemicals capable of killing bacteria, molds, and viruses;
wherein the unitized photocatalytic air sterilizer device is removably attached to an air purifier device, the air purifier device having one or more of: an electrical connection plug to supply power to the unitized air sterilizer device, an air inlet and an air outlet aligned in parallel to the orientation of the plurality of stacked catalytic plates, and a motor driven air mover to drive air through the air inlet and the air outlet and past the unitized air sterilizer device in the direction substantially parallel to the orientation of the plurality of stacked catalytic plates; and
said each of said catalytic plates has a square or rectangular shape with four edges;
said catalytic plates are attached, by one of said four edges, to a plurality of support plates positioned substantially perpendicular to said catalytic plates, wherein each of the plurality of support plates supports a plurality of catalytic plates on one side, thus creating the plurality of stacked parallel catalytic plates with four faces in which each face corresponds to one of said four edges;
in which each of said plurality of support plates is alternately positioned at opposite sides of said catalytic plates so as to provide support on one side for the plurality of stacked parallel catalytic plates without creating a full barrier to the free flow of air in the direction substantially parallel to the orientation of the plurality of stacked catalytic plates and across said plurality of stacked parallel catalytic plates from any one of said four faces.

2. The device of claim 1, wherein said plurality of stacked parallel catalytic plates, said at least one electronic UV light source, and said electronic circuitry may be simultaneously attached or detached from the air purifier device at the same time.

3. The device of claim 2, wherein said air purifier device further comprises a HEPA filter, and in which said HEPA filter filters air prior to exposure to the unitized air sterilizer device.

4. The device of claim 1, in which said electronic circuitry is capable of using a range of AC input voltages spanning at least 100 V to 240 Volts, and 50 Hz to 60 Hz, to power said at least one electronic UV light.

5. The device of claim 1, in which said at least one electronic UV light source is at least one UV germicidal lamp with a fluorescent tube form factor, and said electronic circuitry comprises at least one electrical ballast for said at least one UV germicidal lamp.

6. The device of claim 1, in which each catalytic plate is a square, the length of the sides of the square are approximately 40 to 100 mm, the separation between successive stacked catalytic plates is between 2 mm and 10 mm, and each individual support plate is attached to between 2 and 11 consecutively stacked parallel catalytic plates.

7. The device of claim 1, in which the catalytic semiconductor outer coating comprises titanium dioxide, and in which the catalytic plate is constructed from a non-catalytic base material selected from the group consisting of metals and plastics.

8. The device of claim 7, in which the catalytic semiconductor coating additionally comprises a hydrophilic or hydroscopic agent capable of absorbing water from water vapor present in air, and presenting said absorbed water to the catalytic semiconductor.

9. The device of claim 7, in which the catalytic semiconductor coating additionally comprises an antimicrobial metallic compound selected from the group consisting of copper, rhodium, and silver.

10. A unitized photocatalytic air sterilizer device, comprising:
a plurality of stacked parallel catalytic metal plates, each said catalytic metal plate having a central opening, thus creating a plurality of stacked central openings;
in which said each of said catalytic metal plates has a square or rectangular shape with four edges;
all of said catalytic metal plates are the same size and shape;
said catalytic metal plates are attached, by one of said four edges, to a plurality of support plates positioned substantially perpendicular to said catalytic metal plates, thus creating the plurality of stacked parallel catalytic metal plates with four faces in which each face corresponds to one of said four edges;
in which each of said plurality of support plates is alternately positioned at opposite sides of said catalytic metal plates so as to provide support on one side for the plurality of stacked parallel catalytic metal plates without creating a full barrier to the free flow of air in the direction substantially parallel to the orientation of the plurality of stacked catalytic plates and across said plurality of stacked parallel catalytic metal plates from any one of said four faces, wherein each of the plurality of support plates supports the plurality of catalytic plates on one side;
at least one electronic UV light source positioned inside said plurality of stacked central openings so that said at least one electronic UV light source spans said plurality of stacked central openings;
electronic circuitry capable of powering said at least one electronic UV light source using a range of AC input voltages spanning at least 100 V to 240 Volts, and 50 Hz to 60 Hz;
wherein said catalytic metal plates comprise a metal base and a catalytic outer coating comprising titanium dioxide; and
said catalytic outer coating comprising titanium dioxide being chosen so as to catalytically react with UV light energy produced by said electronic UV light source, and trace amounts of water vapor in the air, and produce oxidizing chemicals capable of killing bacteria, molds, and viruses.

11. The device of claim 10, wherein said unitized air sterilizer device may be attached or detached to an air purifier device comprising one or more of the following:
a HEPA filter;
an electrical connection plug to supply power to said unitized air sterilizer device; and
a motor driven air mover to drive air past said unitized air sterilizer device in the direction substantially parallel to the orientation of the plurality of stacked catalytic plates and;
wherein said plurality of stacked parallel catalytic metal plates, said at least one electronic UV light source, and said electronic circuitry may be simultaneously attached or detached from the air purifier device at the same time.

12. The device of claim 11, wherein said air purifier device contains a holder for said unitized air sterilizer device configured so that air must first pass through the HEPA filter, and then through the unitized air sterilizer device, and then through the motor driven air mover, before the air can then exit the device.

13. The device of claim 11, wherein said unitized air sterilizer device may be attached or detached to said air purifier device using a hand operated clip or plug.

14. The device of claim 10, wherein said unitized air sterilizer device is a disposable device intended to be used, discarded, or recycled as a unit.

15. The device of claim 10, wherein said at least one electronic UV light source emits UV light with wavelengths between about 185 nm and 254 nm.

16. A unitized photocatalytic air sterilizer device, comprising:
a plurality of stacked parallel catalytic metal plates, each said catalytic metal plate having a central opening, thus creating a plurality of stacked central openings;
in which said each of said catalytic metal plates has a square or rectangular shape with four edges;
all of said catalytic metal plates are the same size and shape;
said catalytic metal plates are attached, by one of said four edges, to a plurality of support plates positioned substantially perpendicular to said catalytic metal plates, thus creating the plurality of stacked parallel catalytic metal plates with four faces in which each face corresponds to one of said four edges;
in which each of said plurality of support plates is alternately positioned at opposite sides of said catalytic metal plates so as to provide support on one side for the plurality of stacked parallel catalytic metal plates without creating a full barrier to the free flow of air in the direction substantially parallel to the orientation of the plurality of stacked catalytic plates and across said plurality of stacked parallel catalytic metal plates from any one of said four faces, wherein each of the plurality of support plates supports the plurality of catalytic plates on one side;

at least one electronic UV germicidal lamp with a fluorescent tube form factor positioned inside said plurality of stacked central openings so that said at least one electronic UV germicidal lamp spans said plurality of stacked central openings;

electronic ballast circuitry capable of powering said at least one electronic UV germicidal lamp;

said electronic ballast circuitry is capable of using a range of AC input voltages spanning at least 100V to 240 Volts, and 50 Hz to 60 Hz, to power said electronic UV fluorescent lamp;

wherein said catalytic metal plates comprise a metal base and a catalytic outer coating comprising titanium dioxide;

said catalytic outer coating comprising titanium dioxide being chosen so as to catalytically react with UV light energy produced by said at least one electronic UV germicidal lamp, and trace amounts of water vapor in the air, and produce oxidizing chemicals capable of killing bacteria, molds, and viruses.

17. The device of claim 16, wherein said unitized air sterilizer device may be removably attached to an air purifier device comprising one or more of:

a HEPA filter;

an electrical connection plug to supply power to said unitized air sterilizer device; and a motor driven air mover to drive air past said unitized air sterilizer device air in the direction substantially parallel to the orientation of the plurality of stacked catalytic plates;

wherein said plurality of stacked parallel catalytic metal plates, said at least one electronic UV germicidal lamp with a fluorescent tube form factor, and said electronic circuitry may be simultaneously attached or detached from the air purifier device at the same time; and wherein said unitized air sterilizer device is a disposable device intended to be used, discarded, or recycled as a unit.

18. The device of claim 17, wherein said air purifier device contains a holder for said unitized air sterilizer device configured so that air must first pass through the HEPA filter, and then through the unitized air sterilizer device, and then through the motor driven air mover, before the air can then exit the device; and wherein said unitized air sterilizer device may be attached or detached to said air purifier device using a hand operated clip or plug.

19. The device of claim 16, in which each catalytic metal plate is a square, the length of the sides of the square are approximately 40 to 100 mm, the separation between successive stacked catalytic metal plates is between 2 mm and 10 mm, the central opening is an approximately circular central opening with a diameter between about 10 and 30 mm, and each individual support plate is attached to between 2 and 11 consecutively stacked parallel catalytic metal plates.

* * * * *